(12) United States Patent
Sato et al.

(10) Patent No.: US 7,160,462 B2
(45) Date of Patent: Jan. 9, 2007

(54) ELUENT FOR ION CHROMATOGRAPHY FOR MEASURING ALKALINE EARTH METAL IONS, AND METHOD FOR ANALYZING ALKALINE EARTH METAL IONS, EMPLOYING IT

(75) Inventors: Shinji Sato, Shinnanyo (JP); Yutaka Ogura, Shinnanyo (JP)

(73) Assignee: Tosoh Corporation, Yamaguchi-ken (JP)

( * ) Notice: Subject to any disclaimer, the term of this patent is extended or adjusted under 35 U.S.C. 154(b) by 70 days.

(21) Appl. No.: 10/675,976

(22) Filed: Oct. 2, 2003

(65) Prior Publication Data

US 2004/0067598 A1 Apr. 8, 2004

Related U.S. Application Data

(62) Division of application No. 10/093,508, filed on Mar. 11, 2002, now abandoned.

(30) Foreign Application Priority Data

Mar. 13, 2001 (JP) ................................ 2001-70358

(51) Int. Cl.
*B01D 15/08* (2006.01)
(52) U.S. Cl. .................... 210/635; 210/656; 210/198.2; 436/161
(58) Field of Classification Search ................ 210/635, 210/656, 198.2; 436/161, 178; 422/70
See application file for complete search history.

(56) References Cited

U.S. PATENT DOCUMENTS

| 3,732,146 A | 5/1973 | Heimburger | 195/66 B |
| 4,259,447 A | 3/1981 | Hafeli | 435/215 |
| 4,381,346 A | 4/1983 | Huasin | 435/215 |
| 4,673,733 A | 6/1987 | Chandra | 210/656 |
| 4,978,620 A | 12/1990 | Morii | 435/226 |

FOREIGN PATENT DOCUMENTS

| JP | A-6-1850 | 1/1994 |
| JP | 6213881 | 8/1994 |
| JP | A-8-257419 | 10/1996 |

OTHER PUBLICATIONS

Hajos: Histidine as a dipolar eluent component in cation chromatography, *Journal of Chromatography A*, 789 (1997) pp. 141-148.
Hajos et al: "Histidine as a dipolar eluent component in cation chromatography II. Prediction of retention data for alkaline and alkaline-earth ions," *Journal of Chromatography A*, 920 (2001) pp. 23-30.
Schomburg et al, "Ion chromatography of alkali and alkaline earth metal ions", *Am. Lab.* (Fairfield Conn.), vol. 21, No. 5, May 1989, pp. 92-101.

*Primary Examiner*—Ernest G. Therkorn
(74) *Attorney, Agent, or Firm*—Nixon & Vanderhye P.C.

(57) ABSTRACT

An eluent for ion chromatography for analyzing divalent cations, which comprises an acid and at least one amino acid selected from the group consisting of histidine, lysine and arginine.

2 Claims, 2 Drawing Sheets

ELUENT FOR ION CHROMATOGRAPHY FOR MEASURING ALKALINE EARTH METAL IONS, AND METHOD FOR ANALYZING ALKALINE EARTH METAL IONS, EMPLOYING IT

This application is a divisional of application Ser. No. 10/093,508 filed Mar. 11, 2002.

The present invention relates to an eluent for ion chromatography for analyzing cations such as alkaline earth metal ions, and an analytical method by ion chromatography employing it.

Heretofore, for analyses of inorganic ions, ion chromatography has been used in many cases, to carry out analyses of ions in environmental water, industrial water related to atomic power/semiconductors and test samples of e.g. food products.

In an analysis of cations by ion chromatography, a separation column packed with a strongly acidic cation exchanger is used. In a case where a column of this type is employed for simultaneously analyzing monovalent cations and divalent cations including alkaline earth metals, there has been a problem that due to a substantial difference in its selectivity, it takes a long time for their analysis, or the analysis has to be carried out by setting an independent analytical condition for each of them. If the analysis is carried out by setting such different analytical conditions, there has been a problem that under the analytical condition for analysis of monovalent cations, divalent cations tend to accumulate in the column, whereby the separation performance deteriorates.

Under the circumstances, there has been a proposal for an improved method for simultaneously analyzing monovalent and divalent cations by ion chromatography. For example, an improved method has been proposed wherein a dilute acid such as dilute nitric acid, or one having a complex-forming agent incorporated to the acid, is used as an eluent. By this improved method, divalent cations are separated in a state where the apparent electrical charge in ion exchange is reduced by formation of a complex with the complex-forming agent or ion exchange group, whereby a chromatogram can be obtained wherein the respective ions are eluted in a good balance in a short period of analytical time. Further, as another improved method for analyzing monovalent and divalent cations simultaneously and satisfactorily, an improved method has also been reported wherein using a weakly acidic cation exchange column, an eluent having a complex-forming agent such as pyridine-2,6-dicarboxylic acid added, is used (Am. Lab. (Fairfield Conn.) Vol. 21, No. 5, p. 92–101). Still further, a weakly acidic cation exchange column for simultaneously analyzing monovalent and divalent cations without using a complex-forming agent, has also been reported (JP-A-6-18505, JP-A-8-257419).

However, the above-mentioned improved methods have a problem that, although the elution may be facilitated, the divalent cations elute in a competitive state of ion exchange equilibrium and complex-formation equilibrium, whereby the peak shape tends to have tailing, as is different from monovalent cations which elute by a normal ion exchange reaction. Consequently, it is not possible to solve problems such as a decrease in the quantifying precision in the analysis of the chromatogram, difficulty in identification due to an overlapping with adjacent peaks and deterioration of the detection sensitivity. Further, depending upon the type of the complex-forming agent, a system peak (a peak not attributable to cations in the test sample) will appear and will overlap the peaks of the test sample, and in order to avoid this, it has been necessary to extend the analytical time.

Under these circumstances, it is an object of the present invention to provide an eluent containing a complex-forming agent, which is capable of letting an alkaline earth metal such as magnesium or calcium elute in a good peak shape and which is capable of not permitting a system peak to appear or not permitting an influence over the analysis of cations.

The present invention has been made to accomplish the above object, and firstly, it provides an eluent for ion chromatography for analyzing divalent cations, which comprises an acid and at least one amino acid selected from the group consisting of histidine, lysine and arginine.

Secondly, the present invention provides such an eluent, wherein the divalent cations are alkaline earth metal ions.

Thirdly, the present invention provides such an eluent, wherein the acid is nitric acid, sulfuric acid, phosphoric acid, methanesulfonic acid, oxalic acid, tartaric acid, benzoic acid or phthalic acid.

Fourthly, the present invention provides a method for analyzing cations by ion chromatography employing a cation exchange column, wherein the eluent as defined above is used.

DESCRIPTION OF THE PERFERRED EMBODIMENTS

Figure 1:
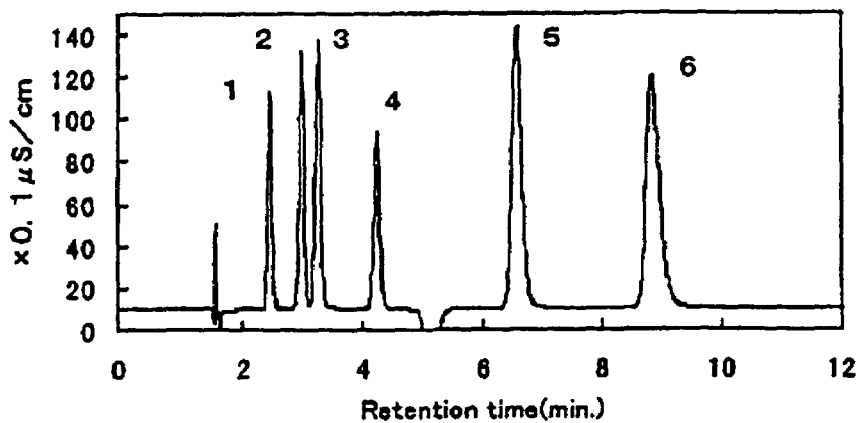
FIG. 1 is a chromatogram showing the results of Example 1. In the figure, the peak 1 is a peak of lithium ions, peak 2 is a peak of sodium ions, peak 3 is a peak of ammonium ions, peak 4 is a peak of potassium ions, peak 5 is a peak of magnesium ions, and peak 6 is a peak of calcium ions.

The acid as one of the components of the eluent, may, for example, be a mineral acid such as nitric acid, sulfuric acid or phosphoric acid, or an organic acid such as methanesulfonic acid, oxalic acid, tartaric acid, benzoic acid or phthalic acid. The concentration of the acid may optionally be determined taking into consideration various conditions such as the ion species to be analyzed and the amount of the test sample to be supplied to the column, but usually, it is preferably from about 0.1 to 10 mmol/l.

In the present invention, at least one amino acid selected from the group consisting of histidine, lysine and arginine is added to the above acid to obtain an eluent in order to elute divalent cations, particularly alkaline earth metal ions, in a good peak shape and further to prevent appearance of a system peak. The amino acid to be added to the above-mentioned acid is at least one member selected from histidine, lysine and arginine, and the respective amino acids are not particularly limited with respect to the types of optical isomers or the purities, and further they are not restricted with respect to the types of counter ions. Such counter ions which are not restricted in the present invention, may, for example, be halide ions such as chloride ions, sulfate ions, nitrate ions or phosphate ions. The concentration of the amino acid to be added to the above acid may also suitably be determined taking into consideration the ion species to be analyzed and various conditions such as the amount of the test sample to be supplied to the column, but it is usually preferably from 0.01 to 10 mmol/l. Further, in a case where two or more amino acids are to be added, the total concentration of the two or more amino acids is preferably within the above range.

The method for analyzing cations by ion chromatography employing a cation exchange column, according to the present invention, is a method in which the eluent having an amino acid added to an acid, as described above, is used. This analytical method is useful for an analysis of divalent cations or for an analysis of a test sample containing monovalent and divalent cations, and it is particularly useful for a test sample containing alkaline earth metal ions as the divalent cations.

The present invention can be carried out by using a conventional column which is commonly used in ion chromatography, such as a separation column packed with a strongly acidic cation exchanger. An example of a commercially readily available column may be TSKgel IC-Cation or TSKgel IC-Cation I/II HR (each being a tradename, manufactured by TOSOH CORPORATION), Shodex YK-421 (tradename, manufactured by Showa Denko K.K.), or Ion-Pac CS12 (tradename, manufactured by Dionex). Among them, it is preferred to employ a column having carboxyl groups introduced to a polymer gel (such as TSKgel IC-Cation I/IIHR) from such a viewpoint that alkali metal ions and alkaline earth metal ions can be eluted in a good balance. It is, of course, possible to use a column having a suitable cation exchange gel packed in a suitable column, other than a commercially available separation column.

The analysis is particularly preferably carried out under conditions such that separation of the respective ions in the separation column is optimized. Such conditions include, for example, the flow rates of the test sample and the eluent, the temperature for analysis, the column capacity (the ion exchange capacity), the amount of the test sample charged and the concentration of the test sample. Usually, it is preferred to carry out a preliminarily analysis by setting the flow rate to be from 0.5 to 1.0 ml/min, the temperature for analysis to be from 25 to 40° C., the amount of the sample charged to be at most 100 µl and the concentration of the test sample to be at most 50 mg/l as the total ion concentration, and then determine the conditions. Detection of cations eluted from the column upon supply of the eluent, can be carried out by using e.g. an electrical conductivity detector, an ultraviolet and visible ray detector or a refractive index detector. However, for a high sensitivity analysis, it is particularly preferred to carry out the detection by means of an electrical conductivity detector.

Now, the present invention will be described in further detail with reference to Examples. However, it should be understood that the present invention is by no means restricted to such specific Examples.

EXAMPLE 1

The following analysis was carried out by using as a column for separation of cations a commercially available column (TSKgel IC-Cation I/II HR, tradename, manufactured by TOSOH CORPORATION, internal diameter: 4.6 mm, length: 10 cm) and as an eluent an eluent containing 2.5 mmol/l of nitric acid and 0.5 mmol/l of histidine. The conditions for the analysis were such that the column temperature was 40° C., and the flow rate of the eluent was 0.67 ml/min, and an electrical conductivity detector was used for the detection.

As a test sample, a mixed aqueous solution (20 µl) was used which contained six types of standard cations ((1) lithium ions (1 mg/l), (2) sodium ions (5 mg/l), (3) ammonium ions (5 mg/l), (4) potassium ions (10 mg/l), (5) magnesium ions (5 mg/l), and (6) calcium ions (10 mg/l)). The obtained chromatogram is shown in FIG. 1.

As is evident from FIG. 1, the time required for the six types of standard cations to appear was about 10 minutes. Further, in FIG. 1, the asymmetry factor of calcium ions was 1.55, and a system peak appeared as a negative peak at about 5.2 minutes and did not hinder quantitative determination of standard cations. Thus, sufficient effects of improvement were obtained.

EXAMPLE 2

A chromatogram was obtained in the same manner as in Example 1 except that as an eluent, an eluent containing 2.5 mmol/l of nitric acid and 0.2 mmol/l of arginine, was used. The obtained chromatogram is shown in FIG. 2.

Figure 2:
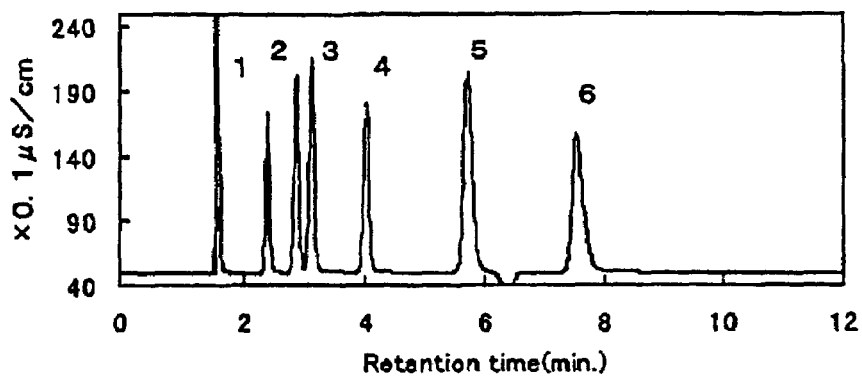
FIG. 2 is a chromatogram showing the results of Example 2. In the figure, peaks 1 to 6 are the same as in FIG. 1.

In FIG. 2, the asymmetry factor of calcium ions was 1.52, and a system peak appeared as a negative peak at about 6.4 minutes and did not hinder quantitative determination of standard cations. Thus, sufficient effects of improvement were obtained.

EXAMPLE 3

A chromatogram was obtained in the same manner as in Example 1 except that as an eluent, an eluent containing 2.5 mmol/l of nitric acid and 0.5 mmol/l of lysine, was used. The obtained chromatogram is shown in FIG. 3.

Figure 3:
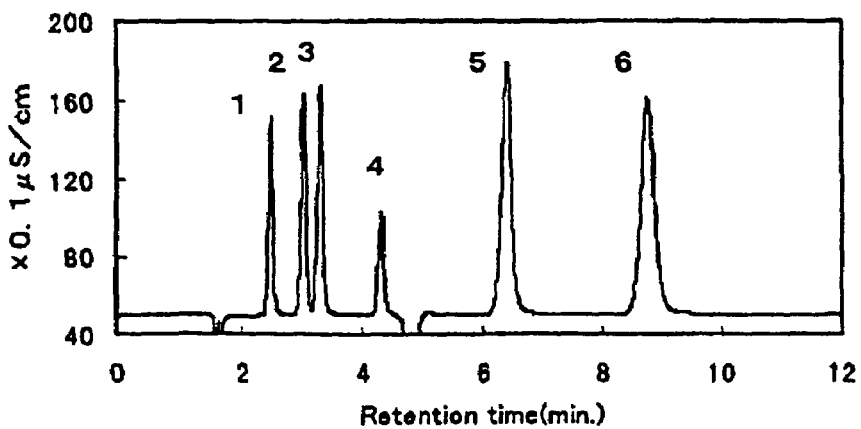
FIG. 3 is a chromatogram showing the results of Example 3. In the figure, peaks 1 to 6 are the same as in FIG. 1.

In FIG. 3, the asymmetry factor of calcium ions was 1.04, and a system peak appeared as a negative peak at about 4.7 minutes and did not hinder quantitative determination of standard cations. Thus, sufficient effects of improvement were obtained.

COMPARATIVE EXAMPLE 1

A chromatogram was obtained in the same manner as in Example 1 except that as an eluent, 2.5 mmol/l of nitric acid was used without adding an amino acid. The obtained chromatogram is shown in FIG. 4.

Figure 4:
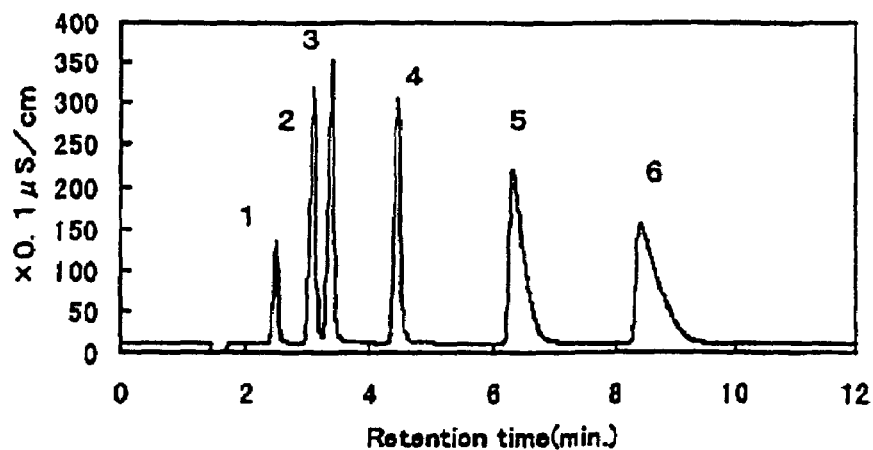
FIG. 4 is a chromatogram showing the results of Comparative Example 1. In the figure, peaks 1 to 6 are the same as in FIG. 1.

In FIG. 4, no system peak appeared, but the asymmetry factor of calcium ions was 5.92, and the peak shape had a large tailing.

COMPARATIVE EXAMPLE 2

A chromatogram was obtained in the same manner as in Example 1 except that as an eluent, 2.5 mmol/l of nitric acid and 0.1 mmol/l of ethylenediamine were used. The obtained chromatogram is shown in FIG. 5.

Figure 5:
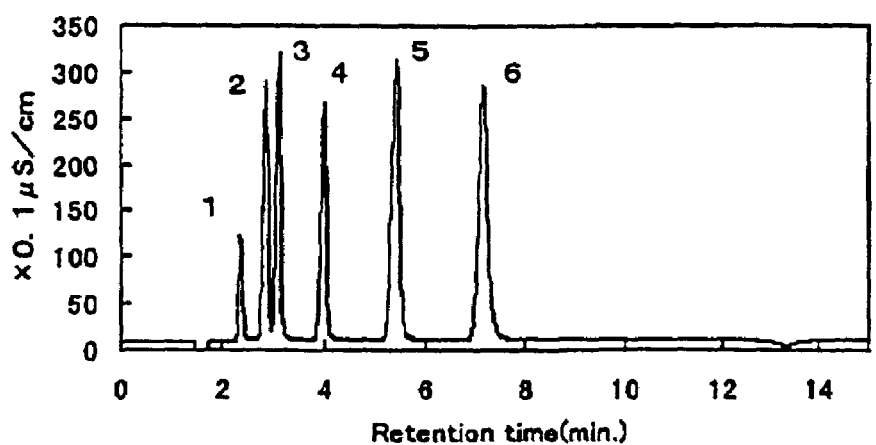
FIG. 5 is a chromatogram showing the results of Comparative Example 2. In the figure, peaks 1 to 6 are the same as in FIG. 1.

In FIG. 5, the asymmetry factor of calcium ions was 0.97, and the effects of improvement of the peak shape was observed. However, a system peak appeared as a negative peak at about 13.4 minutes, and-therefore, the analysis cycle had to be at least 14 minutes. Consequently, the total analytical time per test sample as prolonged.

COMPARATIVE EXAMPLE 3

A chromatogram was obtained in the same manner as in Example 1 except that as an eluent, an eluent containing 2 mmol/l of nitric acid and 1 mmol/l of pyridine-2,6-dicarboxylic acid was used. The obtained chromatogram is shown in FIG. 6.

Figure 6:
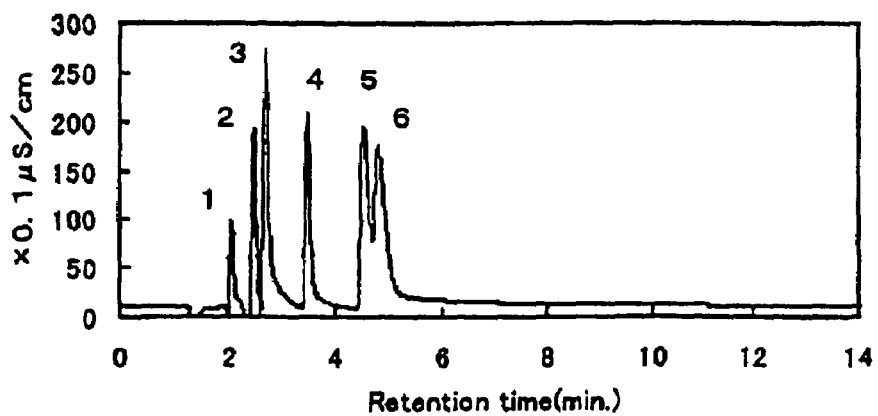
FIG. 6 is a chromatogram showing the results of Comparative Example 3. In the figure, peaks 1 to 6 are the same as in FIG. 1.

In FIG. 6, the asymmetry factor of calcium ions was 2.2, and the effects of improvement of the peak shape were observed, but a system peak appeared as a broad positive peak between 2 minutes to 4 minutes and overlapped the peaks of standard cations, whereby quantitative determination of the standard cations became difficult.

As described in the foregoing, by the eluent of the present invention, it becomes possible to elute alkaline earth metals such as magnesium and calcium in good peak shapes and to make a system peak not to influence over the analysis. Further, the present invention can be carried out by using a conventional means such as a column as it is, and it can be carried out simply by adding an acid to an amino acid, whereby no additional load will be required to the person in its practical operation.

The entire disclosure of Japanese Patent Application No. 2001-70358 filed on Mar. 13, 2001 including specification, claims, drawings and summary are incorporated herein by reference in its entirety.

What is claimed is:

1. A method for analyzing alkaline earth metal ions by ion chromatography, consisting of the steps of
   (a) eluting a cation exchange column with an eluent which comprises an acid selected from the group consisting of nitric acid, sulfuric acid, phosphoric acid, methanesulfonic acid, oxalic acid, tartaric acid, benzoic acid and phthalic acid and at least one amino acid selected from the group consisting of histidine, lysine and arginine,
   (b) detecting cations eluted from the column upon supplying the eluent, and
   (c) preparing a chromatogram.

2. A method for analyzing alkaline earth metal ions by ion chromatography, consisting of the steps of
   (a) eluting a cation exchange column with an eluent which consists essentially of an acid selected from the group consisting of nitric acid, sulfuric acid, phosphoric acid, methanesulfonic acid, oxalic acid, tartaric acid, benzoic acid and phthalic acid and at least one amino acid selected from the group consisting of histidine, lysine and arginine,
   (b) detecting cations eluted from the column upon supplying the eluent, and
   (c) preparing a chromatogram.

* * * * *